(12) United States Patent
Keller et al.

(10) Patent No.: US 11,357,924 B2
(45) Date of Patent: Jun. 14, 2022

(54) CONTROLLER FOR A MEDICAMENT DELIVERY DEVICE

(71) Applicant: SHL MEDICAL AG, Zug (CH)

(72) Inventors: Christian Keller, Taipei (TW); Pei Chi Hu, New Taipei (TW); Shih Hsun Tu, Taoyuan (TW)

(73) Assignee: SHL MEDICAL AG, Zug (CH)

(*) Notice: Subject to any disclaimer, the term of this patent is extended or adjusted under 35 U.S.C. 154(b) by 149 days.

(21) Appl. No.: 16/337,689

(22) PCT Filed: Oct. 5, 2017

(86) PCT No.: PCT/EP2017/075367
§ 371 (c)(1),
(2) Date: Mar. 28, 2019

(87) PCT Pub. No.: WO2018/069150
PCT Pub. Date: Apr. 19, 2018

(65) Prior Publication Data
US 2020/0030538 A1  Jan. 30, 2020

(30) Foreign Application Priority Data
Oct. 13, 2016  (EP) .................................. 16193794

(51) Int. Cl.
*A61M 5/31* (2006.01)
*A61M 5/315* (2006.01)
(52) U.S. Cl.
CPC ... *A61M 5/3157* (2013.01); *A61M 2205/3317* (2013.01); *A61M 2205/3569* (2013.01)

(58) Field of Classification Search
CPC .. A61M 5/3157; A61M 5/2033; A61M 5/178; A61M 5/31571; A61M 5/31573;
(Continued)

(56) References Cited

U.S. PATENT DOCUMENTS 5,080,648 A * 1/1992 D'Antonio .......... A61M 5/2425
604/135
5,760,577 A 6/1998 Shizuya
(Continued)

FOREIGN PATENT DOCUMENTS

CN 1150646 A 5/1997
CN 1684729 A * 10/2005 ........ A61M 5/14546
(Continued)

OTHER PUBLICATIONS

International Search Report and Written Opinion for Int. App. No. PCT/EP2017/075367, dated Dec. 13, 2017.
(Continued)

*Primary Examiner* — William R Carpenter
(74) *Attorney, Agent, or Firm* — McDonnell Boehnen Hulbert & Berghoff LLP

(57) ABSTRACT

A medicament delivery device and a controller is disclosed. The medicament delivery device includes a medicament container, plunger rod and a resilient member. The plunger rod is in contact with a slidable stopper within the medicament container for expelling a medicament. The resilient member is used for applying a force to the plunger rod upon a delivery of the medicament. In addition, the controller is configured to detect a completion of a delivery stroke of the plunger rod according to an inductive property of the resilient member.

15 Claims, 3 Drawing Sheets

(58) Field of Classification Search
CPC .......... A61M 5/31575; A61M 5/31576; A61M 5/31578; A61M 2205/3317; A61M 2205/3569; A61M 5/31565; A61M 5/31566; A61M 5/31568

See application file for complete search history.

(56) References Cited

U.S. PATENT DOCUMENTS

| | | | | |
|---|---|---|---|---|
| 2008/0312604 | A1* | 12/2008 | Boesen | A61M 5/31568 604/207 |
| 2013/0317434 | A1 | 11/2013 | Fabien et al. | |
| 2015/0343152 | A1* | 12/2015 | Butler | A61M 5/31551 604/207 |
| 2016/0012205 | A1* | 1/2016 | Saint | H04B 7/24 604/154 |
| 2016/0129187 | A1* | 5/2016 | Roervig | A61M 5/31553 604/207 |
| 2017/0007765 | A1* | 1/2017 | Cowe | A61M 5/172 |
| 2017/0333637 | A1* | 11/2017 | Merz | A61M 5/28 |

FOREIGN PATENT DOCUMENTS

| | | | | | |
|---|---|---|---|---|---|
| CN | 102209568 | A | | 10/2011 | |
| CN | 202802378 | U | | 3/2013 | |
| CN | 104428019 | A | | 3/2015 | |
| DE | 102016208635.9 | | * | 5/2016 | ............. A61M 5/28 |
| EP | 2583710 | A1 | | 4/2013 | |
| EP | 3215203 | A1 | * | 9/2017 | .......... A61M 5/2033 |
| GB | 2446059 | A | | 7/2008 | |
| JP | H09-5188 | A | | 1/1997 | |
| JP | 2011-507668 | A | | 3/2011 | |
| JP | 2012-519028 | A | | 8/2012 | |
| JP | 2013528107 | A | | 7/2013 | |
| JP | 2015520643 | A | | 7/2015 | |
| JP | 2015520643 | A | * | 7/2015 | |
| WO | 2009/083600 | A1 | | 7/2009 | |
| WO | 2010/098931 | A1 | | 9/2010 | |
| WO | 2011/156373 | A1 | | 12/2011 | |
| WO | 2014/209591 | A2 | | 12/2014 | |
| WO | 2015/066522 | A1 | | 5/2015 | |
| WO | 2015/187793 | A1 | | 12/2015 | |
| WO | WO-2015185311 | A1 | * | 12/2015 | .......... A61M 5/2033 |
| WO | WO-2017108272 | A1 | * | 6/2017 | .......... A61M 5/5086 |

OTHER PUBLICATIONS

Chinese Office Action for CN Application No. 201780059583.7 dated Nov. 16, 2020.

English translation of Japanese Office Action for JP Application No. 2019-520080, dated Jun. 23, 2020 .

* cited by examiner

CONTROLLER FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/075367 filed Oct. 5, 2017, which claims priority to European Patent Application No. 16193794.1 filed Oct. 13, 2016. The entire disclosure contents of these applications are herewith incorporated by reference into the present application.

TECHNICAL FIELD

The present disclosure is directed to a controller for a medicament delivery device, in particular, is directed to a controller configured to detect a completion of a medicament delivery.

BACKGROUND

Advanced medicament delivery devices have been developed in a user-friendly way featured with automatic mechanisms. The advanced automatic medicament delivery devices are designed mechanically to achieve an audible, tactile or visual confirmation of injection completion such that users can use them more intuitively and ergonomically with less risk of human errors.

Document EP 2583710A describes such an advanced automatic medicament delivery device. As described in EP 2583710A, an automatic injection is initialized while a user presses the proximal end of the medicament delivery device, thereby enabling the needle to penetrate the injection area. The medicament delivery device then provides an audible sound to indicate to the user that the injection is completed. In this way, the advanced automatic medicament delivery device allows a user to easily accomplish the process of the injection.

However, a mechanical medicament delivery device may not be very precise and adaptive. For example, an audible confirmation of this mechanical medicament delivery device may not correspond to precise timing of injection completion and also may not be adjustable/customizable for indication of a progress of medicament delivery.

SUMMARY

The present disclosure is directed to a controller for a medicament delivery device. The medicament delivery device comprises a medicament container, a plunger rod and a resilient member. The plunger rod is in contact with a slidable stopper within the medicament container for expelling a medicament. The resilient member is used for applying a force to the plunger rod upon a delivery of the medicament. In addition, the controller is configured to detect a completion of a delivery stroke of the plunger rod according to an inductive property of the resilient member.

Preferably, the inductive property is derived by the frequency variation of the resilient member during the delivery of the medicament.

Preferably, the frequency variation is regarding a resonance frequency derived from a LC circuit including the resilient member.

Preferably, the resilient member is coil shaped and corresponds to an inductive element of the LC circuit.

Preferably, a monitoring of a resonance frequency value of the LC circuit is activated at a time when the delivery of the medicament begins and the resonance frequency value is continuously monitored in order to determine the completion of the stroke of the plunger rod.

Preferably, the completion of the stroke of the plunger rod is determined when the resonance frequency value is detected to be equal to or more than a predetermined frequency value.

Preferably, a monitoring of a resonance frequency difference per unit time of the LC circuit is activated at a time when the delivery of the medicament begins and the resonance frequency difference per unit time is continuously monitored until the completion of the stroke of the plunger rod.

Preferably, the completion of the stroke of the plunger rod is determined at a time when the resonance frequency difference per unit time is substantially equal to 0.

Preferably, the controller controls an indicator to indicate a progress of the medicament delivery.

Preferably, the controller is configured to send a signal to the indicator for indicating the completion of the stroke of the plunger rod and wherein the indicator is configured to indicate the completion of the delivery of the medicament after a predetermined delay time.

Preferably, the medicament delivery device further includes a communication unit configured to communicate with the controller and with an external unit.

Preferably, the indicator is located within the medicament delivery device and/or the external unit.

Preferably, the predetermined delay time is customizable.

According to the present disclosure, the provided medicament delivery device could be customizable to precisely detect the completion of the delivery of the medicament and the controller of the medicament delivery device could be configured to control an indicator to indicate the entire progress of the medicament delivery.

Further features and aspects of the present disclosure will become apparent from the following detailed description of embodiments with reference to the attached drawings.

BRIEF DESCRIPTION OF THE DRAWINGS

The accompanying drawings, which are incorporated in and constitute a part of the specification, illustrate exemplary embodiments, features, and aspects of the disclosure and, together with the description, serve to explain the principles of the disclosure.

DETAILED DESCRIPTION

Various exemplary embodiments, features, and aspects of the disclosure will be described in detail below with reference to the drawings. For the drawings below, the same or the similar numbers and symbols are referred to the same or the similar elements.

Figure 1:
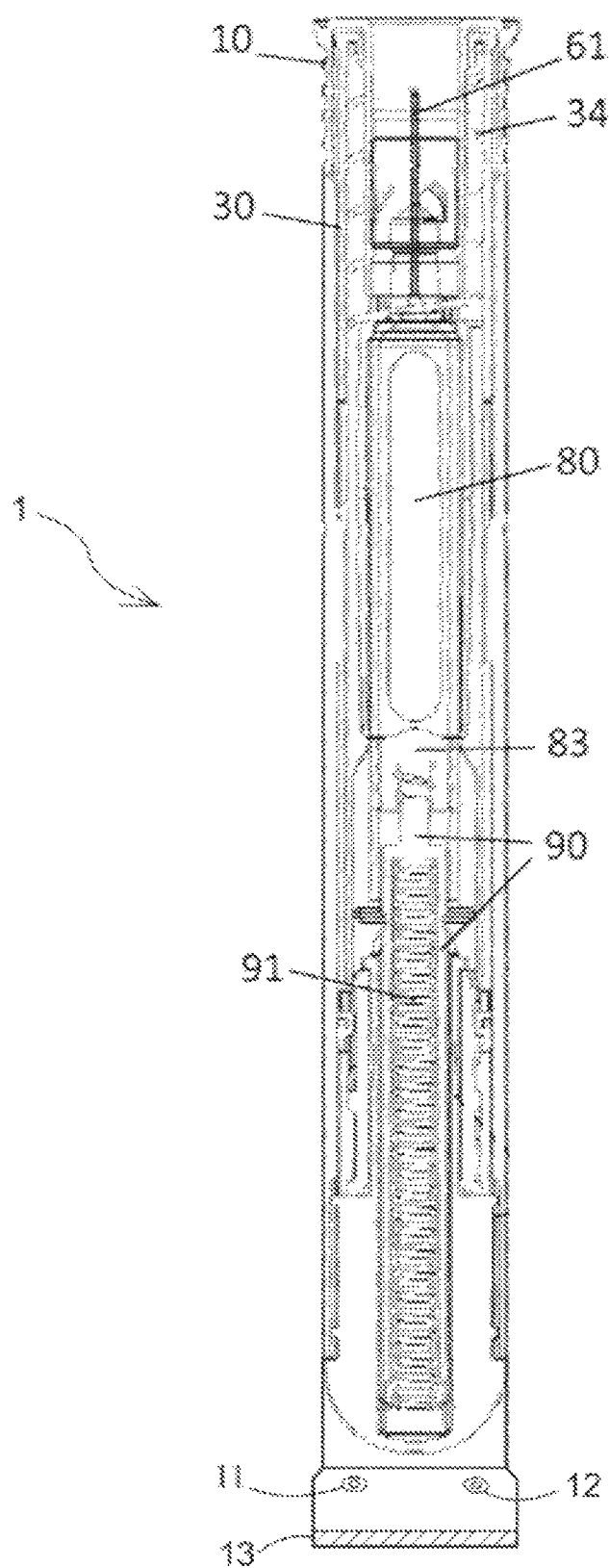
FIG. 1 shows a cross section view of a medicament delivery device in an initial state having a controller, an indicator and a communication unit according to an embodiment of the disclosure.

FIG. 1 shows a cross section view of a medicament delivery device 1 in an initial state having a controller 11, an indicator 13 and a communication unit 12 according to an embodiment of the disclosure. Referring to FIG. 1, the medicament delivery device 1 mainly includes a medicament container 80, a plunger rod 90, a slidable stopper 83, a resilient member 91. The medicament container 80 is arranged within the medicament delivery device 1 and has a predetermined volume to contain a medicament. The plunger rod 90 has a proximal end in contact with the slidable stopper 83 and encloses the resilient member 91 which is adapted to apply a force to the plunger rod 90 in the proximal direction. The slidable stopper 83 is disposed within the medicament container 80 for expelling the medicament.

In addition, the medicament delivery device 1 further includes a cap 10, a tubular activation member 30, a spring 34, a needle 61 and housing members (not shown). When a user removes the cap 10 and presses the tubular activation member 30 against a delivery area (e.g., against the arm skin of the user), the spring 34 is compressed, the needle 61 is penetrated and the housing members are cooperated with the components 80, 90, 83 and 91 to achieve an automatic injection. Meanwhile, the resilient member 91 applies a force to the plunger rod 90 upon the delivery of the medicament. This technique of automatic injection has been already presented e.g., in Document EP 2583710A and is incorporated herein by reference.

According to an embodiment, the controller 11 could be configured or programmed to detect the completion of the delivery stroke of the plunger rod 90. According to an embodiment, the resilient member 91 may be coil shaped or may be a spring and thus the resilient member 91 could be served as an inductor while being implemented in a circuit, i.e., the resilient member 91 has an inductive property. According to an embodiment, the controller 11 could be configured to detect the completion of the delivery stroke of the plunger rod 90 according to the inductive property of the resilient member 91. In addition, the controller 91 could be any available controller which is programmable or configurable.

Figure 2:
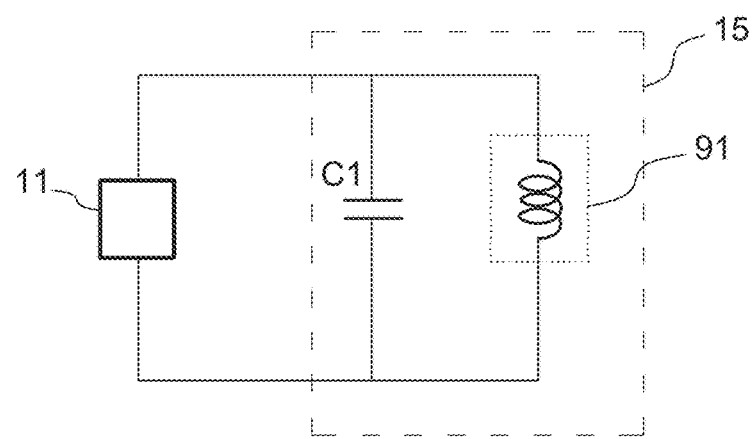
FIG. 2 shows an exemplary schematic LC circuit implemented in the medicament delivery device of FIG. 1 for the detection of the delivery stroke of the plunger rod based on the inductive property of the resilient member, according to an embodiment of the disclosure.

FIG. 2 shows an exemplary schematic LC circuit 15 implemented in the medicament delivery device 1 of FIG. 1 for the detection of the delivery stroke of the plunger rod 90 based on the inductive property of the resilient member 91, according to an embodiment of the disclosure. Referring to both FIGS. 1 and 2, since the resilient member 91 could be served as an inductor, the resilient member 91 could correspond to an inductive element of an inductance-capacitance (LC) circuit, wherein a capacitor C1 could be provided and coupled with the resilient member 91 to form a LC circuit 15. The controller 11 may be coupled to the LC circuit 15 and detect a resonance frequency derived from the LC circuit 15. The resonance frequency could be obtained from the equation:

$$f = \frac{1}{2\pi\sqrt{LC}},$$

where L represents the inductance of the resilient member 91, C represents the capacitance of the capacitor C1 and f represents the resonance frequency.

According to an embodiment, the controller 11 may be configured to always monitor the resonance frequency value of the LC circuit 15. According to another embodiment, the controller 11 may start to monitor the resonance frequency value of the LC circuit 15 at the time when the delivery of the medicament begins; that is, monitoring the resonance frequency value of the LC circuit 15 is triggered or activated when a user presses the proximal end of the medicament delivery device and starts to inject a medicament.

According to an embodiment of the disclosure, the controller 11 may be continuously monitoring the resonance frequency value of the LC circuit 15 during the delivery of the medicament. In other words, the controller 11 keeps detecting the LC circuit 15 when the medicament is being injected. Subsequently, the controller 11 may determine the completion of the stroke of the plunger rod 90 based on a frequency variation of the resilient member 91.

Figure 3:
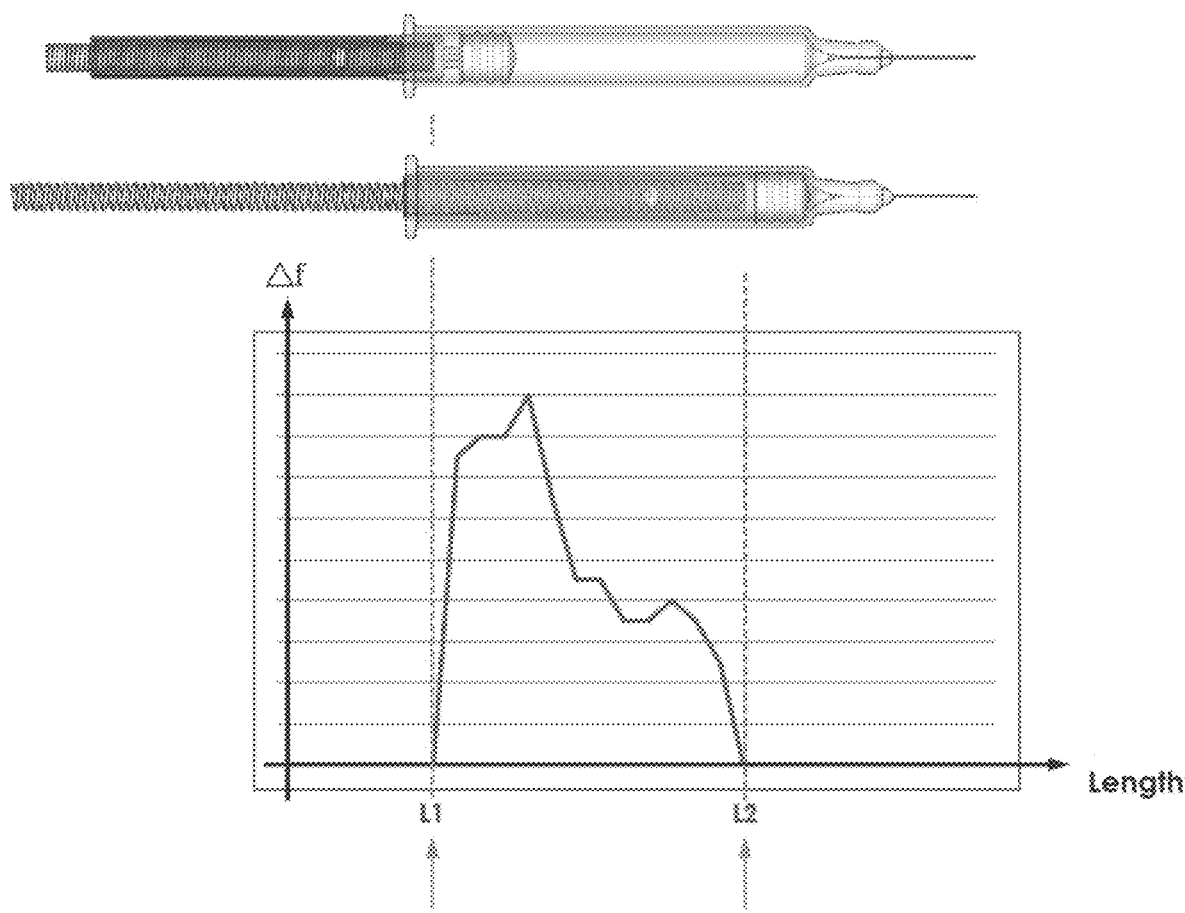
FIG. 3 illustrates a plot of the resonance frequency difference per unit time versus the length of the resilient member.

FIG. 3 illustrates a plot of the resonance frequency difference per unit time versus the length of the resilient member 91. Referring to FIGS. 1-3, while the medicament delivery device 1 is unused or begins to be used, the resilient member 91 is in a pre-tensioned state, i.e., the resilient member 91 is compressed with a length L1. During the injection, the plunger rod 90 is released and the resilient member 91 is increasing length so as to apply forces to the slidable stopper 83 to move, causing the medicament to be delivered. Upon the completion of the delivery stroke of the plunger rod 90, the resilient member 91 stops relaxing and has a length L2.

According to an embodiment of the disclosure, the resilient member 91 is coil shaped with a plurality of helical coils. When the plunger rod 90 is released, the resilient member 91 may change length from L1 to L2 upon relaxing. Meanwhile, each adjacent pair of the coils of the resilient member 91 may be stretched by a distance, causing the inductance variation of the resilient member 91. Consequently, increasing the distance between each adjacent pair of coils may cause reducing the inductance derived from the resilient member 91 so as to cause the resonance frequency of the LC circuit 15 to vary.

According to an embodiment of the disclosure, a predetermined frequency value could be defined by the capacitance of the capacitor C1 and the inductance of the resilient member 91 in the relaxing state with length L2. Accordingly, the controller 11 could determine the completion of the stroke of the plunger rod 90 when the resonance frequency value is detected to be substantially equal to or more than the predetermined frequency value.

According to another embodiment, it may be observed from FIG. 3 that the resonance frequency difference per unit time Δf is varying within the duration that the resilient member 91 is changing length from L1 to L2. Thus, the controller 11 may initiate monitoring the resonance frequency difference per unit time Δf of the LC circuit 15 at the time when the delivery of the medicament begins. Subsequently, the controller 11 could keep monitoring the resonance frequency difference per unit time Δf while the plunger rod 90 is moving and the resilient member 91 is relaxing. Consequently, the controller 11 may determine the completion of the stroke of the plunger rod 90 if the resonance frequency difference per unit time Δf is detected to be substantially equal to 0, i.e., the resonance frequency of the LC circuit 15 stops varying and becomes a constant value.

According to an embodiment of the disclosure, the controller 11 may be wiredly or wirelessly coupled to an indicator. As shown in FIG. 1, the controller 11 may control the indicator 13 to indicate a progress of the medicament delivery of the medicament delivery device 1.

According to an embodiment of the disclosure, the indicator 13 may be located within the medicament delivery device. For example, the indicator 13 which is wiredly coupled to the controller may be, but not limited to, a LED device, a vibration device, a buzzer or speaker or any device which is tangible for a human.

According to another embodiment, an indicator (not shown) which is wirelessly coupled to the controller 11 may be external to the medicament delivery device 1. According to an aspect, an external indicator may be a simple device, such as an external buzzer or speaker, an external vibration device or an external LED device or the like. According to another aspect, an external indicator may be an external electronic device, such as a mobile phone, a smart watch, a smart bracelet or the like. However, an external indicator of the disclosure is not limited to those devices mentioned above. Any device which could receive indicating signals wirelessly from the controller 11 may also be used as an external indicator for the medicament delivery device 1. Additionally, according to an embodiment, the medicament delivery device 1 may further includes a communication unit 12 (as shown in FIG. 1), which may be configured to communicate with the controller 11 and to communicate with an external unit. In this way, the controller 11 may send a signal to an external indicator (not shown) through the communication unit 12.

Figure 4:
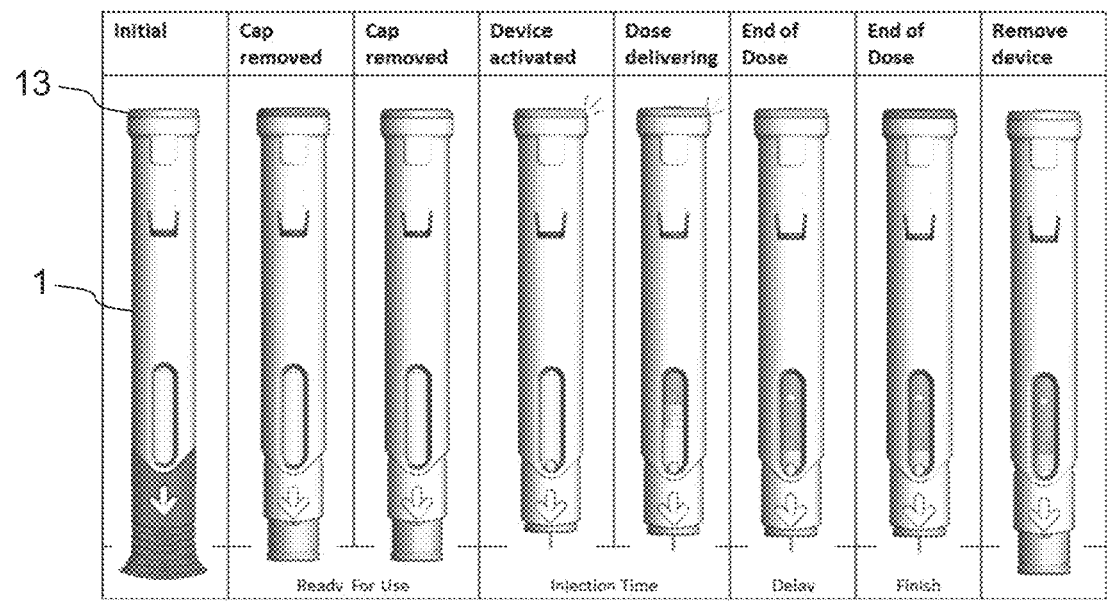
FIG. 4 illustrates an indicator implemented with a medicament delivery device to indicate several phases of a progress of a medicament delivery, according to an embodiment of the disclosure.

FIG. 4 illustrates an indicator 13 implemented with a medicament delivery device 1 to indicate several phases of a progress of a medicament delivery, according to an embodiment of the disclosure. The medicament delivery device 1 of FIG. 4 shows an exterior appearance of the medicament delivery device 1 of FIG. 1 that a user may see, wherein the indicator 13 may be e.g., a LED device 13.

Referring to FIG. 4, the medicament delivery device 1 is lidded with a cap in an initial phase. After the cap is removed, the LED device 13 may emit light for a while to indicate that the medicament delivery device 1 is ready for use (a phase of ready-for-use). After the delivery of the medicament is activated, the LED device 13 of the medicament delivery device 1 may start to blink; and the LED device 13 may keep blinking during the delivery of the medicament/dose (a phase of injection). Until the completion of the stroke of the plunger rod (not shown) of the medicament delivery device 1 is determined as mentioned above, the LED device 13 may stop blinking but still emit light for a delay time (a phase of time delay). The LED device 13 may emit light with a different color after the delay time has passed to indicate the real completion of the delivery of the medicament (a phase of finish). After the medicament delivery device 1 is removed (e.g., from a human body), the LED device 13 may stop emitting light.

Regarding the phase of injection, the injection time may depend upon the power source (e.g., battery) of the medicament delivery device 1, properties of the syringe of the medicament delivery device 1 (such as size or material), an amount of medicament/drug, viscosity of medicament/drug, the needle gauge of the medicament delivery device 1 and/or combination thereof. Accordingly, a normal condition of injection time could be determined within a predetermined range before injection. Thus, the controller of the medicament delivery device 1 could also determine a failure condition of injection. For example, if the injection time is too short, the controller of the medicament delivery device 1 may determine that the medicament delivery device 1 is mal-functioned (or jammed). On the other hand, if the injection time is too long, the controller of the medicament delivery device 1 may determine that the plunger rod of the medicament delivery device 1 is moving too slow due to e.g., wear-out.

As to the phase of delay time, because the medicament is usually still delivering when the delivery stroke of the plunger rod has completed, the completion of the delivery of the medicament may happen after the delivery stroke of the plunger rod finishes. Thus, there is latency between the completion of the delivery stroke of the plunger rod and the completion of the delivery of the medicament. In other words, the final completion time of the delivery of the medicament approaches to the completion time of the delivery stroke of the plunger rod plus a delay time. According to an embodiment, the delay time may be predetermined depending upon human body (who is the target subjected to be injected) properties, medicament parameters, the medicament delivery device design and/or external condition. For example, the human body properties may be, but not limited to, blood pressure, injection site, injection temperature, skin pressure/resistance, body fat percentage, hydration condition, age and etc.; the medicament parameters may be, but not limited to, viscosity, dosage and etc.; the medicament device design may be, but not limited to, needle gauge, needle length, injection spring power and etc.; and the external environmental condition may be, but not limited to, storage temperature and etc. Accordingly, the predetermined delay time is customizable for each individual human body under each individual injection environment.

Figure 5:
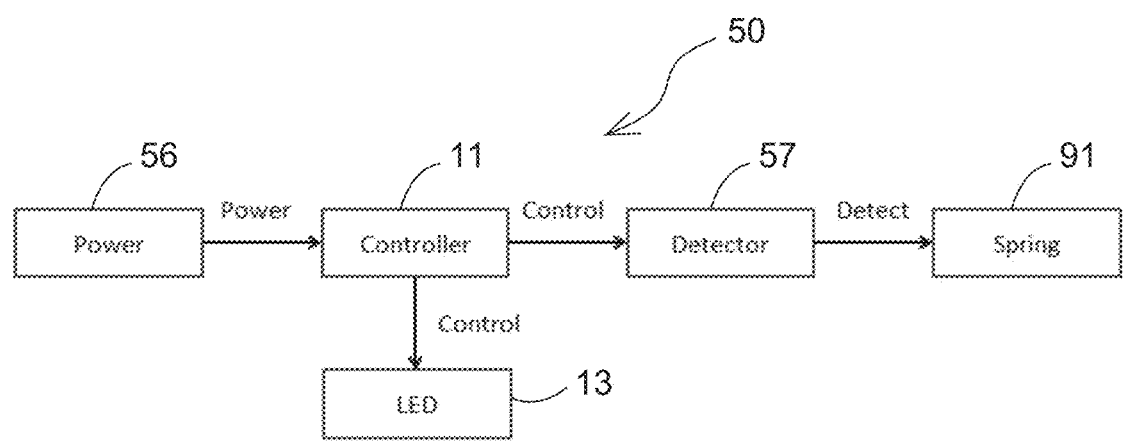
FIG. 5 shows a functional block diagram of a controlling circuit implemented in the medicament delivery device of FIG. 1 according to an embodiment of the disclosure.

FIG. 5 shows a functional block diagram of a controlling circuit 50 implemented in the medicament delivery device of FIG. 1 according to an embodiment of the disclosure. Referring to FIG. 5, the controlling circuit 50 includes a power source 56, a controller 11, a detector 57, a resilient member (spring) 91 and an indicator (LED device) 13. While the medicament delivery device is powered on, the controller 11 receives power from the power source 56, which may be e.g., a battery. According to an embodiment of the disclosure, the controller 11 may control the detector 57 to detect an inductive property (such as resonance frequencies) of the resilient member 91 and the controller 11 could control the indicator 13 to indicate the progress of the usage of the medicament delivery device according to the inductive property of the resilient member 91.

In summary, the present disclosure provides a medicament delivery device with a controller thereof. The medicament delivery device includes a medicament container, a plunger rod and a resilient member. The controller of the medicament delivery device could be configured to sense the inductive property of the resilient member to determine the completion of the delivery stroke of the plunger rod and further to determine the completion of the delivery of the medicament with a customizable delay time. In addition, the controller also could control an indicator to indicate the entire progress of the delivery of the medicament. As a result, a precise, customizable and more intuitive medicament delivery device is achieved.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A medicament delivery device comprising:
a medicament container;
a plunger rod in contact with a slidable stopper within the medicament container for expelling a medicament;
a resilient member used for applying a force to the plunger rod during delivery of the medicament;
a capacitor operatively engaged with the resilient member to thereby form an LC circuit;
a controller in communication with the LC circuit, wherein the controller is configured to detect a completion of a delivery stroke of the plunger rod according to an inductive property of the resilient member derived from the LC circuit; and
an indicator to indicate a progress of delivery of the medicament, wherein the indicator is controlled by the controller,
wherein the inductive property of the resilient member comprises a resonance frequency of the LC circuit,
wherein a monitoring of a resonance frequency difference per unit time of the LC circuit is activated at a time when the delivery of the medicament begins and the resonance frequency difference per unit time is continuously monitored until the completion of the delivery stroke of the plunger rod,
wherein the controller is configured to send a signal to the indicator for indicating the completion of the delivery stroke of the plunger rod,
wherein the indicator is configured to indicate the completion of the delivery stroke of the plunger rod at a time when the resonance frequency difference per unit time is substantially equal to 0 plus a predetermined delay time corresponding to a time between when the plunger rod stops moving and when the last medicament exits the medicament delivery device,
wherein the predetermined delay time is customizable for each individual human body under each individual injection environment,
wherein the controller is configured to determine an injection time based on a time between when the delivery of the medicament begins and the determined completion of the delivery stroke,
wherein the controller is configured to compare the determined injection time to a predetermined injection time range,
wherein, if the controller determines the determined injection time falls within the predetermined injection time range, the controller determines a normal condition of the delivery stroke of the plunger rod, and
wherein, if the controller determines the determined injection time falls outside of the predetermined injection time range, the controller determines a failure condition of the delivery stroke of the plunger rod.

2. The medicament delivery device according to claim 1, wherein the resilient member is coil shaped and corresponds to an inductive element of the LC circuit.

3. The medicament delivery device according to claim 1, wherein a monitoring of a resonance frequency value of the LC circuit is activated at a time when the delivery of the medicament begins and the resonance frequency value is continuously monitored in order to determine the completion of the delivery stroke of the plunger rod.

4. The medicament delivery device according to claim 3, wherein the completion of the delivery stroke of the plunger rod is further determined at a time when the resonance frequency value is detected to be equal to or more than a predetermined frequency value.

5. The medicament delivery device according to claim 1, further comprising:
a communication unit configured to communicate with the controller and with an external unit.

6. The medicament delivery device of claim 5, wherein the external unit comprises one of an external buzzer, an external speaker, an external vibration device, or an external LED device.

7. The medicament delivery device of claim 5, wherein the external unit comprises one of a mobile phone, a smart watch, or a smart bracelet.

8. The medicament delivery device of claim 1, wherein the indicator comprises one of an LED device, a vibration device, a buzzer, or a speaker.

9. The medicament delivery device of claim 1, wherein the customizable predetermined delay time is determined based on one or more human body properties, one or more medicament parameters, one or more design features of the medicament delivery device and/or one or more external conditions.

10. The medicament delivery device of claim 9, wherein the one or more human body properties comprise one or more of a blood pressure, an injection site, an injection temperature, a skin pressure/resistance, a body fat percentage, a hydration condition, and an age of a patient.

11. The medicament delivery device of claim 9, wherein the one or more medicament parameters comprise one or more of a viscosity and a dosage of the medicament.

12. The medicament delivery device of claim 9, wherein the one or more design features of the medicament delivery device comprise one or more of a needle gauge, a needle length, and an injection spring power.

13. The medicament delivery device of claim 9, wherein the one or more external conditions comprise a storage temperature of the medicament.

14. The medicament delivery device of claim 1,
wherein the indicator comprises an LED device,
wherein the LED device emits a first colored light to indicate that the medicament delivery device is ready for use,
wherein the LED device emits a blinking light during the delivery of the medicament,
wherein the LED device emits the first colored light during the predetermined delay time, and
wherein the LED device emits a second colored light after the predetermined delay time, wherein the second colored light is a different color than the first colored light.

15. The medicament delivery device of claim 14,
wherein the LED device emits no light after the medicament delivery device is removed from an injection site.

* * * * *